(12) United States Patent
Hahs et al.

(10) Patent No.: US 7,101,512 B2
(45) Date of Patent: Sep. 5, 2006

(54) CASSETTE AND DELIVERY SYSTEM

(75) Inventors: Michael Hahs, San Clemente, CA (US); Su-Syin Wu, Irvine, CA (US); Edward V. Quoss, Claremount, CA (US)

(73) Assignee: Ethicon, Inc., Somerville, NJ (US)

( * ) Notice: Subject to any disclaimer, the term of this patent is extended or adjusted under 35 U.S.C. 154(b) by 249 days.

(21) Appl. No.: 09/737,399

(22) Filed: Dec. 15, 2000

(65) Prior Publication Data

US 2002/0076357 A1 Jun. 20, 2002

(51) Int. Cl.
*B01L 3/00* (2006.01)

(52) U.S. Cl. .............. 422/102; 422/99; 422/104; 422/292; 206/521; 206/586; 206/588

(58) Field of Classification Search ............ 206/387.11, 206/784, 521, 586, 588, 730, 731; 229/129.1; 422/104, 58
See application file for complete search history.

(56) References Cited

U.S. PATENT DOCUMENTS

| | | | |
|---|---|---|---|
| 3,411,696 A * | 11/1968 | Ayer et al. ............... 206/525 |
| 3,618,848 A * | 11/1971 | Pawlowski et al. ...... 206/485.1 |
| 3,756,384 A | 9/1973 | Stone |
| 3,765,529 A * | 10/1973 | Mueller ................. 206/779 |
| 3,828,922 A * | 8/1974 | Holkestad ............... 206/1.5 |
| 3,874,500 A * | 4/1975 | Nicholl ................. 206/320 |
| 3,933,240 A * | 1/1976 | Humble ................. 206/1.5 |
| 4,026,411 A * | 5/1977 | Johnson ................ 206/589 |
| 4,200,192 A * | 4/1980 | Klomp .................. 206/418 |
| 4,313,540 A * | 2/1982 | Hart et al. .............. 206/588 |
| 4,313,541 A * | 2/1982 | Hart et al. .............. 206/588 |
| 4,445,613 A * | 5/1984 | Cassidy ................. 206/418 |
| 4,550,834 A * | 11/1985 | Fletcher et al. .......... 229/207 |
| 4,643,876 A | 2/1987 | Jacobs et al. |
| 4,674,633 A * | 6/1987 | Steadman ............... 206/521 |
| 4,817,800 A * | 4/1989 | Williams et al. ....... 128/203.15 |
| 4,869,286 A | 9/1989 | Williams et al. |
| D306,065 S * | 2/1990 | Williams et al. .......... D24/217 |
| D306,066 S * | 2/1990 | Williams et al. .......... D24/217 |
| 4,899,519 A * | 2/1990 | Williams et al. ............ 53/412 |
| 4,913,196 A | 4/1990 | Williams et al. |
| D307,794 S * | 5/1990 | Williams et al. .......... D24/217 |
| 4,921,099 A * | 5/1990 | Trauschke .............. 206/418 |
| 4,938,262 A | 7/1990 | Williams et al. |
| 4,941,518 A | 7/1990 | Williams et al. |
| 5,016,262 A | 5/1991 | Cushing |
| 5,242,107 A * | 9/1993 | De Nola ............... 229/120.26 |
| 5,691,530 A | 11/1997 | Solitt |
| 5,839,574 A * | 11/1998 | Lorence et al. .......... 206/216 |
| 5,869,341 A * | 2/1999 | Woodaman ............. 116/206 |
| 5,882,611 A * | 3/1999 | Williams et al. ......... 206/569 |
| 5,887,716 A * | 3/1999 | Williams et al. ............ 141/1 |
| 5,976,881 A * | 11/1999 | Klingner ................. 422/58 |
| 6,412,340 B1* | 7/2002 | Nguyen et al. ............ 73/104 |
| 6,565,802 B1* | 5/2003 | Hanley et al. ............. 422/22 |
| 6,843,408 B1* | 1/2005 | Agren .................. 229/167 |

FOREIGN PATENT DOCUMENTS

| | | |
|---|---|---|
| EP | 0 882 457 A2 | 12/1998 |
| EP | 0 882 458 A2 | 12/1998 |

OTHER PUBLICATIONS

European Search Report EP 01 31 0522 dated Dec. 9, 2002.

* cited by examiner

*Primary Examiner*—Jill Warden
*Assistant Examiner*—Dwayne K Handy

(57) ABSTRACT

A cassette is received within a sleeve having an open end. Specially folded flaps at the open end are applied to center the cassette in the sleeve and to reduce a width of the open end of the sleeve.

8 Claims, 9 Drawing Sheets

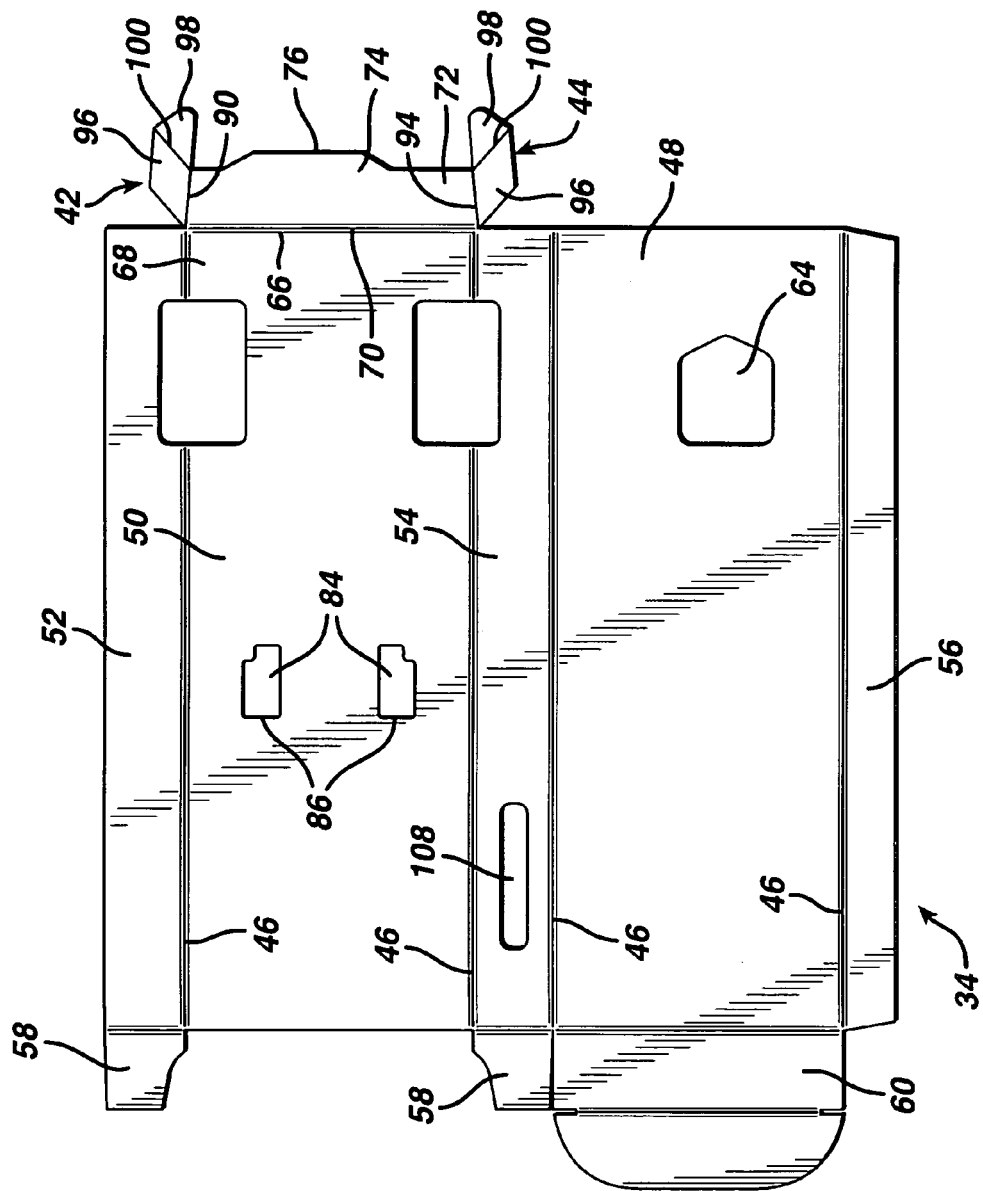

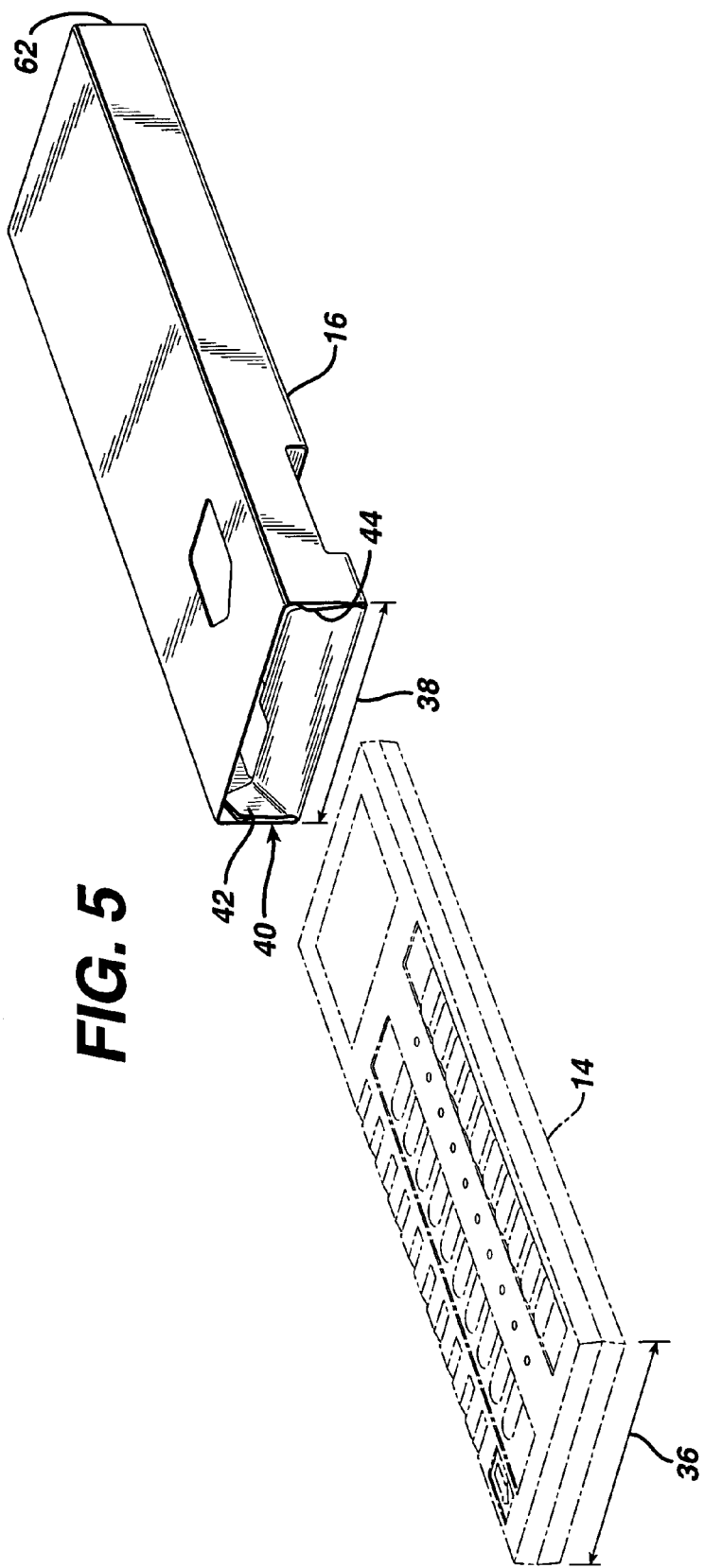

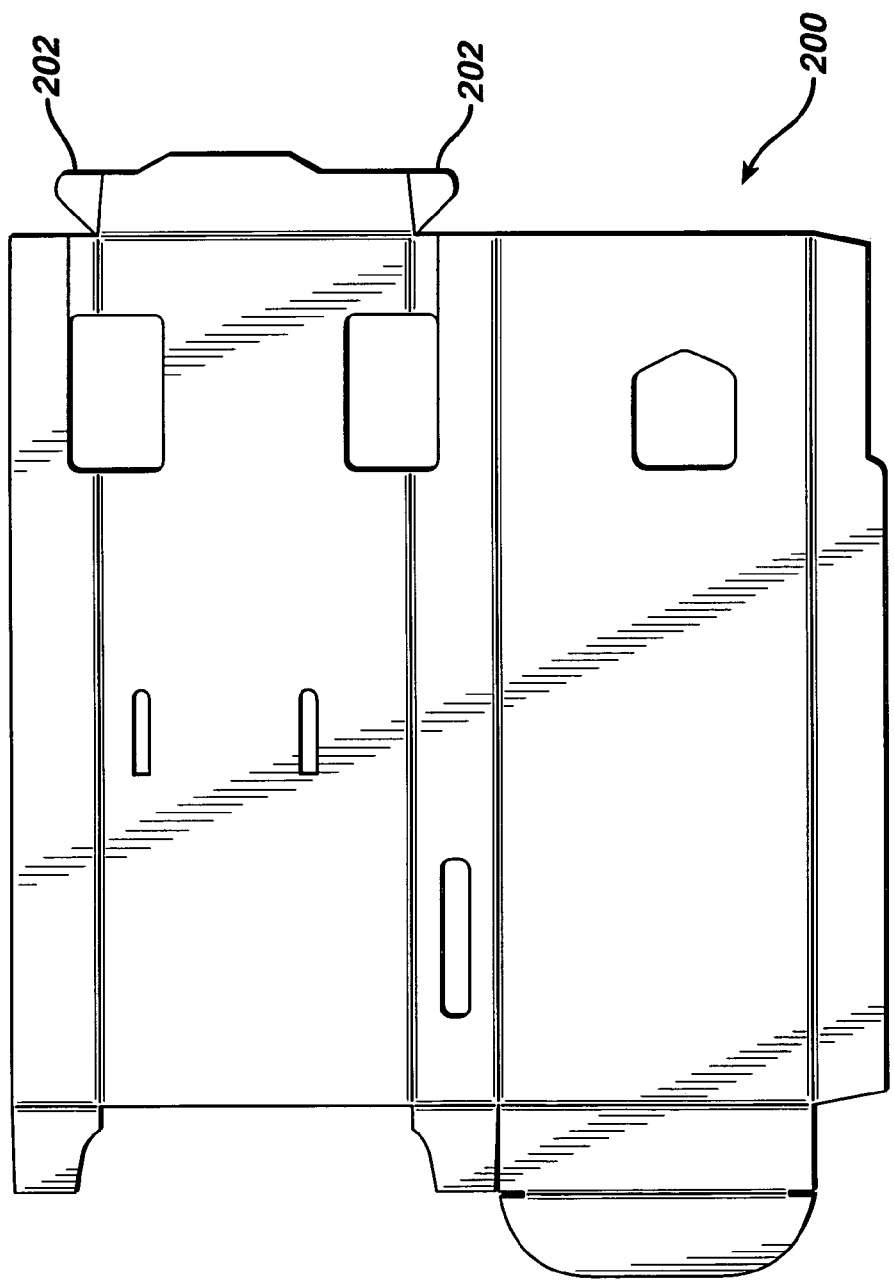

CASSETTE AND DELIVERY SYSTEM

FIELD OF THE INVENTION

The present invention relates to a system for storing and delivering cassettes to a device.

BACKGROUND OF THE INVENTION

U.S. Pat. No. 4,643,876, incorporated herein by reference, discloses a sterilization system in which an agent such as hydrogen peroxide is introduced into a evacuated sterilizing chamber where it is vaporized and allowed to disperse onto the items to be sterilized. After a desired period of time, electrical energy is applied to the chamber to ionize the gas and form a plasma field at a power level sufficient to achieve sterilization.

This system has been successfully commercialized as the STERRAD® Sterilization System and is available from Advance Sterilization Products, Division of Ethicon Endo-Surgery, Inc., Irvine, Calif. The system is used in hospitals and other environments where it is operated repeatedly throughout the day by personnel having a widely varying range of understanding of the apparatus. To ensure simple and automatic operation with adequate safeguards with respect to human error, the system employs an automated delivery system for delivering the liquid sterilant to the sterilization chamber. Measured portions of the sterilant, in this case hydrogen peroxide but many other sterilizing agents could be substituted therefor, are provided in rupturable cells within a rigid cassette housing. A transport system maneuvers the cassette within the STERRAD® sterilizer and releases the given quantity of hydrogen peroxide into the sterilization chamber automatically. One form of cassette and operation of the deliver system are more fully described in the Williams et al. U.S. Pat. No. 4,817,800 issued Apr. 4, 1989; U.S. Pat. No. 4,913,196 issued Apr. 3, 1990; U.S. Pat. No. 4,938,262 issued Jul. 3, 1990; and U.S. Pat. No. 4,941,518 issued Jul. 17, 1990, all of which are incorporated herein by reference.

An improved cassette and delivery system is shown in the Williams et al. U.S. Pat. No. 5,882,611 directed to a sleeve which retains and protects the cassette and U.S. Pat. No. 5,877,716 directed to an indicia system on a cassette sleeve. Each of these patents are incorporated herein by reference. The '611 patent describes a sleeve having an inner layer of corrugated cardboard and an outer layer of pressboard, producing a sleeve of considerable thickness.

The present cassette and sleeve employ a single layer sleeve which eases manufacturing and reduces the expense of the sleeve and employs a pair of folded tabs to accommodate both the present type of cassette and sleeve and that shown in the '611 patent in the same machine by providing that the important external dimensions of the cassette and sleeve can be the same for each system even though the present system employs a sleeve having a different thickness.

SUMMARY OF THE INVENTION

A cassette assembly for delivering a substance according to the present invention comprises a cassette having at least one cell therein containing a quantity of the substance and a protective sleeve covering the cassette. The cassettes has a first side, a second side opposite the first side and a first end and the sleeve has a first side, a second side opposite the first side and a first end. A first tab at the sleeve first end extends inwardly from the first side toward the second side and abuts the cassette's first side. A second tab at the sleeve first end extends inwardly from the second side toward the first side and abuts the cassette's second side. The cassette has a first lateral dimension between its first side and its second side which is smaller than a second lateral dimension between the sleeve first side and the sleeve second side.

Preferably, the cassette further comprises a first face between its first side and its second side and the sleeve further comprises a first edge at its first end between its first side and its second side with the sleeve having a retaining member connected to the sleeve by a hinge at the sleeve first edge and abutting the cassette first face, and with the first tab and the second tab extending inwardly from respective first and second lateral edges of the retaining member.

Preferably, the first and second tabs have at least one flap folded inwardly toward the sleeve sides. Preferably, the sleeve is formed of absorbent stock, as for instance cardboard or a coated cardboard, so that a small quantity of the substance on the cassette can be absorbed into the stock.

An indicator strip can be provided on the sleeve for indicating the presence of substance thereon. Identifying indicia on the cassette can be provided along with and an aperture through the sleeve in registry with the indicia whereby the indicia can be read through the aperture.

A method, according to the present invention, supplies a cassette encased in a sleeve for a machine, the machine having an opening sized to accommodate cassettes having a first fixed dimension between first and second sides thereof and to accommodate sleeves containing the cassettes having a second fixed dimension between first and second sides thereof, the difference between the second and the first dimensions being substantially greater than twice the thickness of the sleeve. The cassette is provided with the first dimension between the first and second sides thereof and the sleeve is provided with the second dimension between the first and second sides thereof. A first tab is folded inwardly from the sleeve first side and a second tab inwardly from the sleeve second side to create a space equaling the first fixed dimension between the first tab and the second tab and the cassette is contained within the sleeve between the first tab and the second tab. Preferably, the cassette is centered in the sleeve between the first and second sides of the sleeve.

BRIEF DESCRIPTION OF THE DRAWINGS

FIG. 4 is a plan view of an unfolded blank for forming the sleeve of FIG. 1;

FIG. 5 is an exploded perspective view of the cassette and sleeve;

FIG. 10 is a plan view of an unfolded blank for forming an alternative embodiment of a sleeve according to the invention.

DETAILED DESCRIPTION OF THE INVENTION

Figure 1:
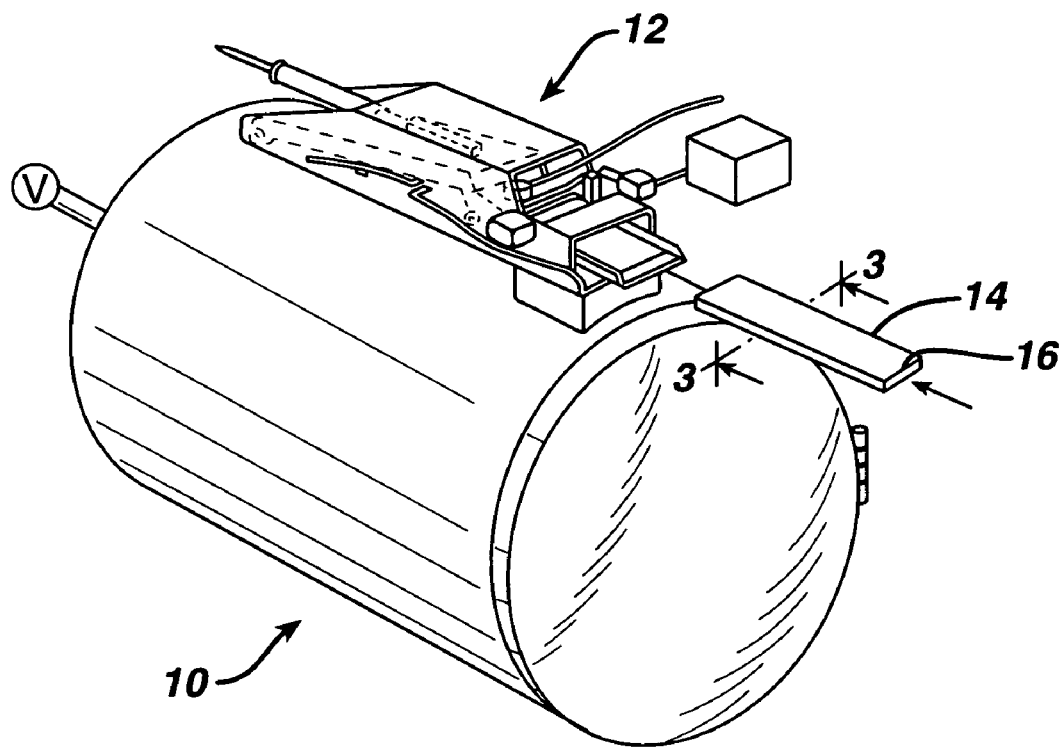
FIG. 1 is a perspective view of a cassette and sleeve according to the present invention, in preparation for entering a sterilization apparatus.
Figure 2:
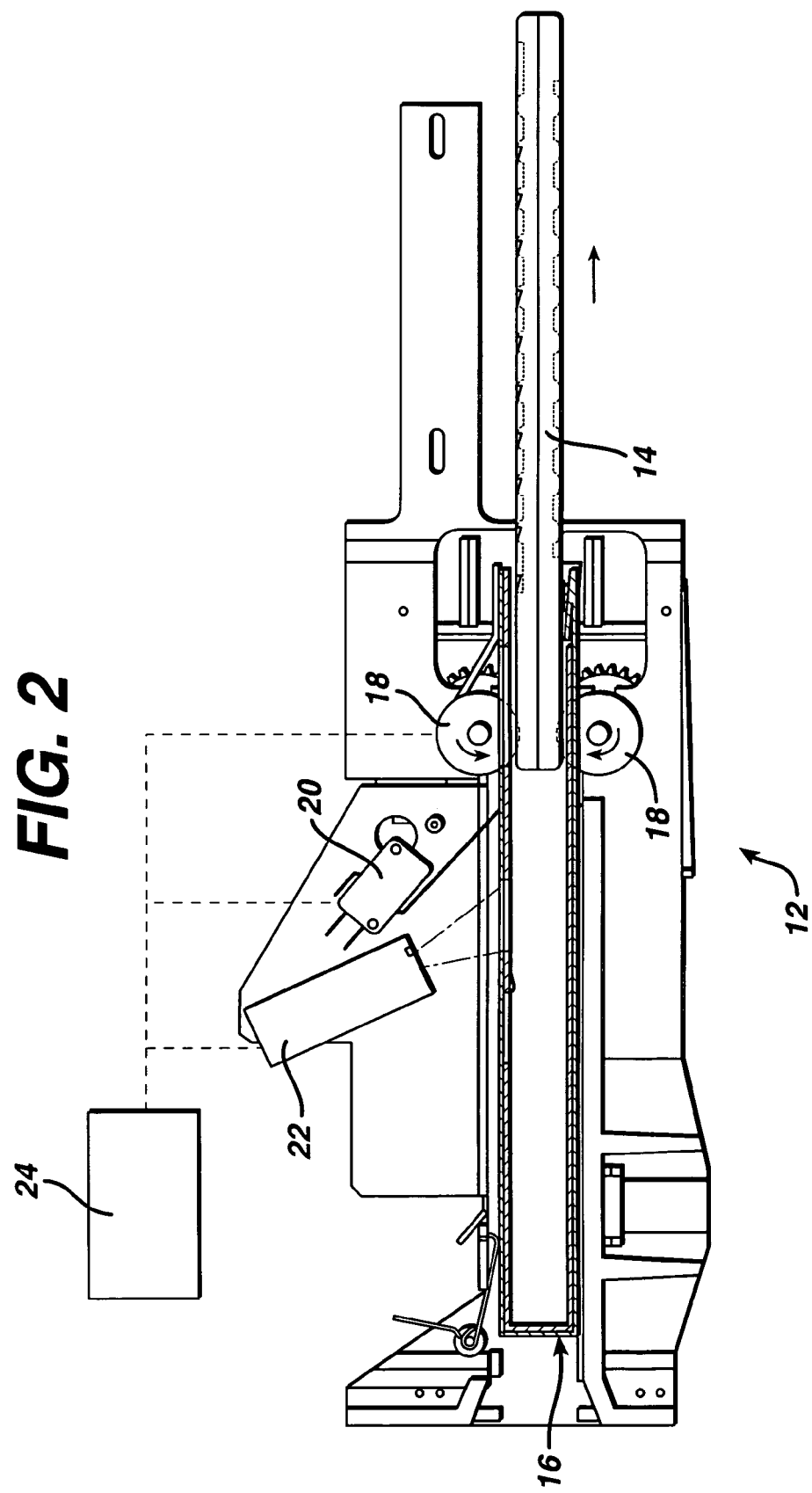
FIG. 2 is a cutaway view of a receiver on the sterilization apparatus of FIG. 1 for receiving the cassette and sleeve of FIG. 1.
Figure 3:
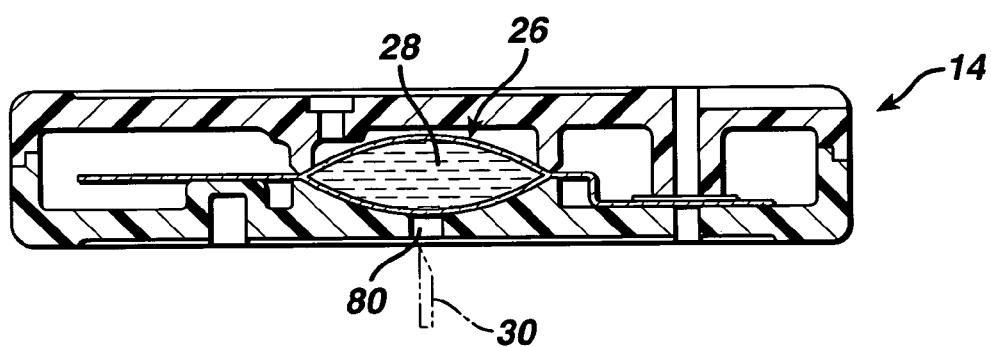
FIG. 3 is a sectional view taken along lines 3—3 of FIG. 1, but showing only the cassette without the sleeve.

FIGS. 1 and 2 illustrate a sterilization or other machine 10 and receiver 12 for receiving a cassette 14. The cassette 14 is received within a protective sleeve 16 which will later be described in more detail. Such a machine and receiver generally comprises a pair of motorized wheels 18 for driving the cassette 14 out of the sleeve 16, a position sensing switch 20 for detecting the presence of the cassette 14 within the receiver 12, a bar code reader 22 or other device for reading indicia (to be described later) on the cassette 14 and a controller 24 for controlling the receiver 12. The cassette 14 has a plurality of cells 26 containing a liquid 28 to be dispensed into the machine 10 (see also FIG. 3) through a hollow piercing needle 30. In the preferred embodiment, the machine 10 is a sterilizer having a sterilization chamber 32 capable of being lowered to subatmospheric pressures, preferable about 10 Torr or less, and the liquid 28 is hydrogen peroxide which vaporizes in the chamber 32 to create a sterilizing vapor. Such systems are described in more detail in the aforementioned patents.

Certain such machines 10 are already commercially available and employ cassettes 14 encased in a thick two layer sleeve such as shown in U.S. Pat. No. 5,882,611. The present cassette 14 is essentially the same as described in the '611 patent. However, the sleeve 16 of the present invention is of a single layer. As shown in FIG. 4, the sleeve 16 is folded from a blank 34 of material such as pressboard or other suitable material and folded into a configuration shown in FIGS. 5 and 6. Preferably, it is absorbent so that after the spent cassette 14 is returned to the sleeve 16 any droplets of the liquid 28 are absorbed by the sleeve 16. However, any number of cellulosic or polymeric materials, coated or uncoated, among others, are suitable for the stock.

The receiver 12 is adapted to receive the cassette 14 having a first fixed lateral dimension 36 and the sleeve having a second wider fixed lateral dimension 38. In the prior cassette/sleeve combinations having a two layer sleeve, the cassette 14 fit closely within the sleeve and the sleeve had a thickness of about 0.086 inch due to its two layer construction employing a layer of corrugated cardboard. Sleeves of a smaller dimension due to a thinner construction would not operate suitably in the receiver 12. Accordingly, the sleeve 16 of the present invention has a unique folded opening 40 with first and second inwardly extending tabs 42 and 44 whereby to provide a sleeve 16 having the same second fixed lateral dimension 38 as the prior sleeves with the two wall construction yet which properly receive the cassette 14 having the first fixed lateral dimension 36. Additionally, the tabs 42 and 44 provide the needed mechanism to center the cassette 14 in the sleeve 16.

Figure 6:
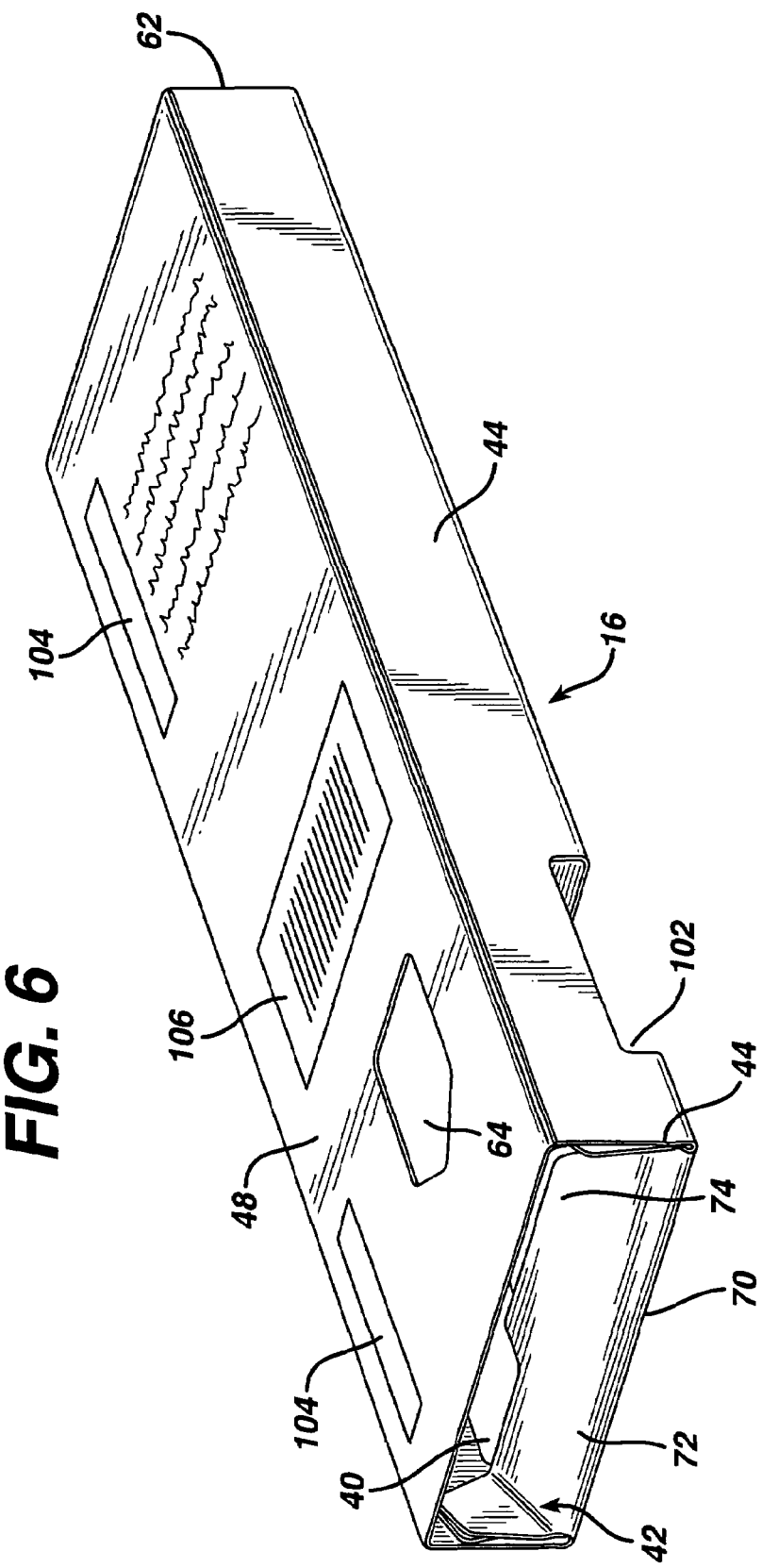
FIG. 6 is a perspective view of the sleeve of FIG. 1.

Turning primarily to FIGS. 4 to 6, longitudinal fold lines 46 form a top panel 48, bottom panel 50, a first side panel 54 and a second side panel 52. The longitudinal fold lines 46 also form a flap 56 which seals to the second side panel 52 to form the three dimensional structure of the sleeve 16. Side tabs 58 and a foldable flap 60 form a closed end 62 of the sleeve 16. An arrow shaped aperture 64 in the sleeve 16 points toward the sleeve open or first end 40.

Figure 7:
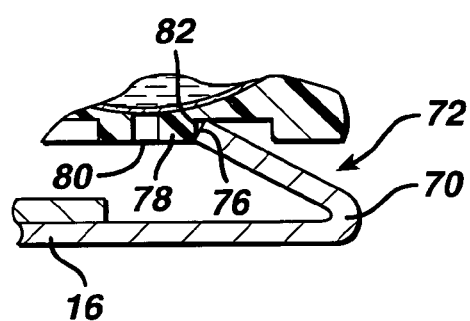
FIG. 7 is a sectional view taken along lines 7—7 of FIG. 1 and showing a retaining tab on the sleeve.

A lateral fold line 66 at a forward end 68 (at the sleeve open end 40) of the bottom panel 50 forms a hinge 70 about which rotates a retaining flap 72. The retaining flap 72 extends from the fold line 66 to terminate in a tang 74, a terminal edge 76 of which engages the cassette 14 to retain the cassette 14 within the sleeve 16. (See also FIG. 7). An annular post 78 surrounds each of a plurality of piercing apertures 80 in the cassette 14 such that each aperture 80 extends axially through the post 78. The post has a vertical annular sidewall 82 against which the terminal edge 76 abuts. The retaining flap 72 holds the cassette 14 within the sleeve 16. Additionally, the tabs 42 and 44 can further reinforce the retaining flap 72 to secure the cassette 14 in the sleeve 16 during shipping or after use. Even fairly vigorous shaking will not dislodge the cassette 14 from the sleeve 16. They are assisted by a pair of central tabs 84 centrally located on the bottom panel 50 which fold inwardly and rearwardly about fold lines 86 to abut an edge (not shown) on the cassette 14 to further hold the cassette 14 within the sleeve 16. Additional functions of central tabs 84 are fully disclosed in the incorporated U.S. Pat. No. 5,882,611.

Figure 8:
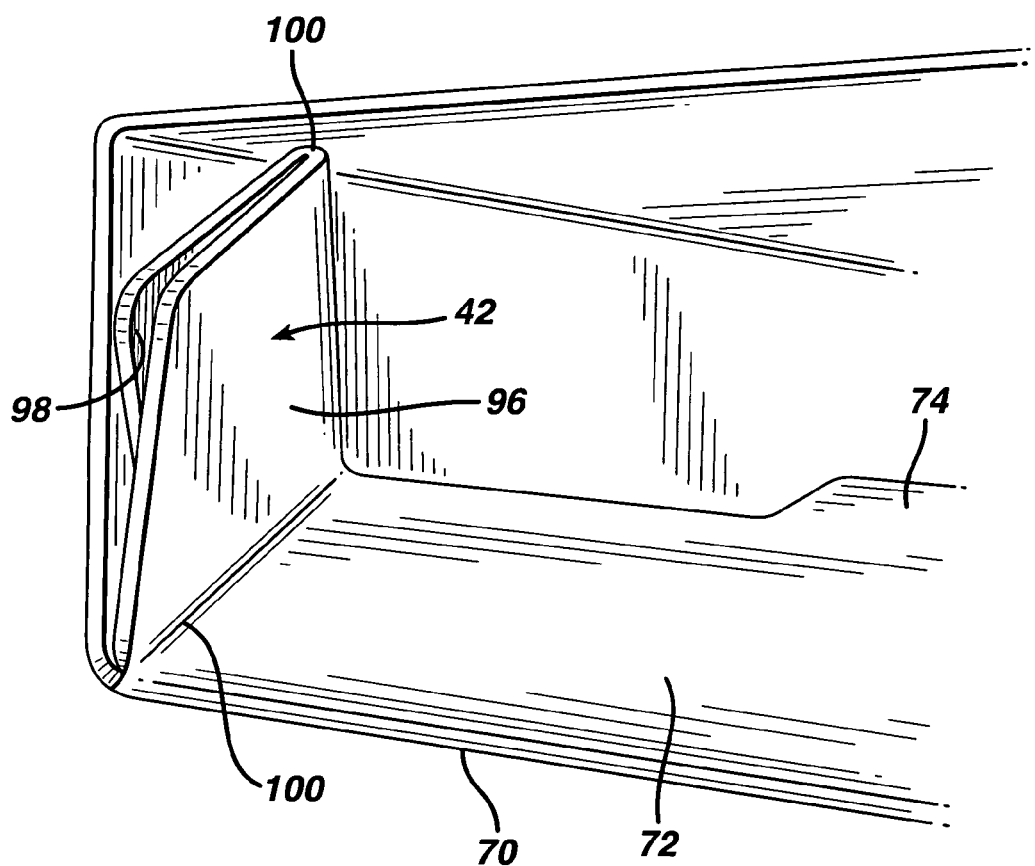
FIG. 8 is a detail view a portion of FIG. 1 showing the folding of tabs on the sleeve.

The first tab 42 extends laterally from a first side 90 of the retaining flap 72 and the second tab 44 extends laterally from a second side 94 of the retaining flap. Each of the first and second tabs 42 and 44 comprise a proximal portion 96 attached to the retaining flap and a distal portion 98 extending forwardly from the proximal portion 96 and separated therefrom by a fold line 100. The proximal portions 96 are folded inwardly toward each other and the distal portions 98 are folded outwardly over the proximal portions 96 as best seen in FIG. 8. This creates the second lateral dimension between the first tab 42 and second tab 44 which accommodates the cassette 14 which has a width slightly smaller than the second lateral dimension.

Figure 9:
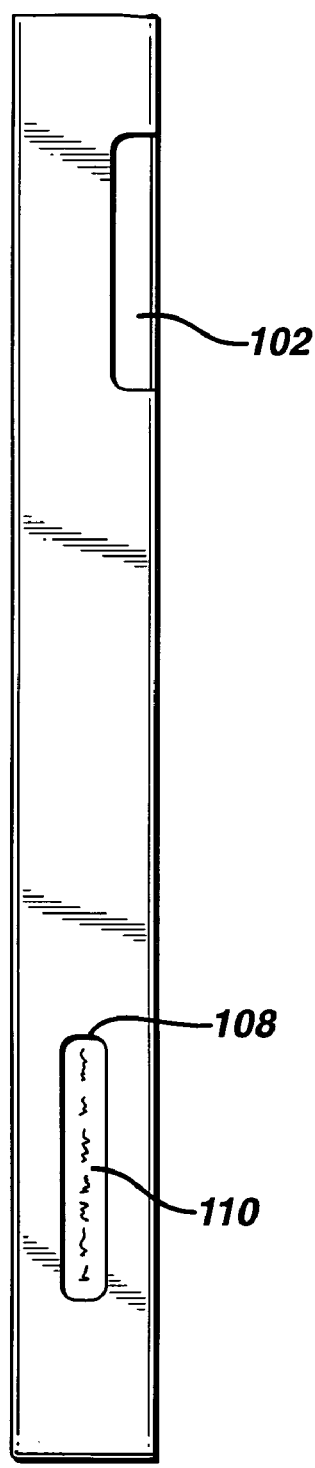
FIG. 9 is a side elevational view of the cassette and sleeve of FIG. 1.

The sleeve 16 contains several additional features, such as openings 102 through the bottom and side panels through which driving wheels (not shown) in the receiver 12 can access the cassette 14. A pair of chemical indicator strips 104 shows whether the sleeve 16 has been exposed to hydrogen peroxide (or, as adapted, to whatever is stored therein). The cassette 14 and sleeve 16 are preferably supplied within a non-permeable overwrap (not shown), such as a sealed clear plastic wrap. If the indicator strips 104 show a color change then the operator knows that the hydrogen peroxide contained in the cassette 14 has leaked and should not open the overwrap. Instructions to this effect are also provided on the sleeve 16. A bar code 106 can provide machine readable information on what is contained in the cassette 14, lot numbers, expiration dates, serial numbers and the like. Each cassette 14 can have a unique identification number or code encoded into the bar code 106. A used cassette 14 can be easily recognized by storing and comparing the unique identification number or code in the memory of the controller 24 each time a cassette 14 is placed in the receiver 12. Used cassettes 14 can thus be rejected. Turning also to FIG. 9, a window 108 through the sleeve 16 can show printed indicia 110 on the cassette 14 indicative of lot numbers and expiration dates and the like.

FIG. 10 illustrates an alternative embodiment of a sleeve 200 according to the present invention. It is similar in most respects to the sleeve 16. However, it employs tabs 202 similar to tabs 42 and 44 but which do not fold upon themselves. They are but a single layer. Of course, the tabs could alternatively be structured to fold more than once so as to produce a tab of three, four or more layers depending upon the thickness of the material and the desired dimensions.

While the invention has been described with regard to a particular embodiment thereof, those skilled in the art will understand, of course, that the invention is not limited thereto since modifications can be made by those skilled in the art, particularly in light of the foregoing teachings. Reasonable variation and modification are possible within the foregoing disclosure of the invention without departing from the spirit of the invention.

What is claimed is:

1. A cassette assembly for delivering a substance, the assembly comprising:
   a cassette having at least one cell therein containing a quantity of the substance, and the cassette further comprising a first side, a second side opposite the first side and a first end between the first side of the cassette and the second side of the cassette;
   a protective sleeve containing the cassette, the sleeve comprising:
      a first side, a second side opposite the first side, a first end between the first side of the sleeve and the second side of the sleeve and a second end opposite the first end of the sleeve, the first end of the sleeve being open for receiving the cassette and the second end of the sleeve being closed;
      a first tab at the first end of the sleeve which extends inwardly from the first side of the sleeve toward the second side of the sleeve and abuts the first side of the cassette;
      a second tab at the first end of the sleeve which extends inwardly from the second side of the sleeve toward the first side of the sleeve and abuts the second side of the cassette; and
   wherein the cassette is positioned within the protective sleeve with the first side of the cassette adjacent the first side of the sleeve and the first end of the cassette at the first end of the sleeve and wherein the cassette has a first lateral dimension defined between its first side and its second side which is smaller than a second lateral dimension defined between the first side of the sleeve and the second side of the sleeve.

2. A cassette assembly according to claim 1 wherein:
   the cassette further comprises a first face between its first side and its second side;
   the sleeve further comprises a first edge at its first end between its first side and its second side;
   the sleeve further comprises a retaining member connected to the sleeve by a hinge at the first edge of the sleeve and abutting the first face of the cassette; and
   wherein the first tab and the second tab extend inwardly from respective first and second lateral edges of the retaining member.

3. A cassette assembly according to claim 2 wherein the first tab further comprises at least one flap folded inwardly toward the first side of the sleeve and the second tab further comprises at least one flap folded inwardly toward the second side of the sleeve.

4. A cassette assembly according to claim 1 wherein the sleeve is formed of absorbent stock, whereby a small quantity of the substance on the cassette can be absorbed into the stock.

5. A cassette assembly according to claim 4 wherein the stock is cardboard.

6. A cassette assembly according to claim 5 wherein the stock is a coated cardboard.

7. A cassette assembly according to claim 1 and further comprising an indicator strip on the sleeve for indicating the presence of substance thereon.

8. A cassette assembly according to claim 7 having identifying an indicia on the cassette and an aperture through the sleeve in registry with the identifying indicia whereby the indicia can be read through the aperture.

* * * * *